(12) United States Patent
Frankel et al.

(10) Patent No.: US 9,023,087 B2
(45) Date of Patent: May 5, 2015

(54) PERCUTANEOUS MODULAR HEAD-TO-HEAD CROSS CONNECTOR

(71) Applicant: Blackstone Medical, Inc., Lewisville, TX (US)

(72) Inventors: Bruce Frankel, Mount Pleasant, SC (US); Mark Evald Semler, McKinney, TX (US); Clinton Walker, Frisco, TX (US); Sergey Fedorov, Plano, TX (US)

( * ) Notice: Subject to any disclaimer, the term of this patent is extended or adjusted under 35 U.S.C. 154(b) by 361 days.

(21) Appl. No.: 13/672,928

(22) Filed: Nov. 9, 2012

(65) Prior Publication Data
US 2014/0135839 A1 May 15, 2014

(51) Int. Cl.
*A61B 17/70* (2006.01)

(52) U.S. Cl.
CPC ......... *A61B 17/7032* (2013.01); *A61B 17/7037* (2013.01); *A61B 17/7049* (2013.01)

(58) Field of Classification Search
CPC ........... A61B 17/7037; A61B 17/7038; A61B 17/7032
USPC ......................................... 606/250–253, 308
See application file for complete search history.

(56) References Cited

U.S. PATENT DOCUMENTS

| | | | |
|---|---|---|---|
| 5,885,286 A * | 3/1999 | Sherman et al. | 606/270 |
| 6,224,598 B1 * | 5/2001 | Jackson | 606/305 |
| 6,485,491 B1 * | 11/2002 | Farris et al. | 606/250 |
| 6,676,661 B1 * | 1/2004 | Martin Benlloch et al. | 606/264 |
| 7,163,538 B2 * | 1/2007 | Altarac et al. | 606/86 A |
| 7,204,838 B2 * | 4/2007 | Jackson | 606/270 |
| 7,645,294 B2 * | 1/2010 | Kalfas et al. | 606/250 |
| 7,691,145 B2 * | 4/2010 | Reiley et al. | 623/17.11 |
| 7,717,939 B2 | 5/2010 | Ludwig et al. | |
| 7,833,251 B1 * | 11/2010 | Ahlgren et al. | 606/279 |
| 7,896,902 B2 * | 3/2011 | Jeon et al. | 606/246 |
| RE42,545 E * | 7/2011 | Ralph et al. | 606/266 |
| 8,012,184 B2 * | 9/2011 | Schlapfer et al. | 606/264 |
| 8,100,909 B2 * | 1/2012 | Butler et al. | 606/60 |
| 8,197,512 B1 * | 6/2012 | Hunt et al. | 606/246 |
| 8,758,411 B1 * | 6/2014 | Rayon et al. | 606/259 |
| 8,852,241 B2 * | 10/2014 | Datta | 606/279 |
| 2003/0004512 A1 | 1/2003 | Farris et al. | |
| 2003/0199873 A1 * | 10/2003 | Richelsoph | 606/61 |

(Continued)

OTHER PUBLICATIONS

International Search Report and Written Opinion, PCT/US2013/069262, dated Mar. 28, 2014, 13 pages.

*Primary Examiner* — Eduardo C Robert
*Assistant Examiner* — Stuart S Bray
(74) *Attorney, Agent, or Firm* — Baker & McKenzie LLP

(57) ABSTRACT

A modular head-to-head cross connector or construct extension system comprising a fastener element driven into a bone in a first orientation, a first U-shaped body operable to receive the fastener element and operable to receive a first rod in a first rod receiving channel, and a first compression element driven adjacent to and against the first rod in the first rod receiving channel, thereby engaging the first rod against the fastener element in a second orientation independent of the first orientation of the fastener element. The system further comprises a second U-shaped body operable to receive first compression element and operable to receive a second rod in a second rod receiving channel, and a second compression element driven adjacent to and against the second rod in the second rod receiving channel, thereby engaging the second rod against the first compression element in a third orientation independent of the second orientation.

21 Claims, 7 Drawing Sheets

(56) References Cited

U.S. PATENT DOCUMENTS

| | | | |
|---|---|---|---|
| 2004/0116928 A1* | 6/2004 | Young et al. | 606/61 |
| 2005/0240265 A1* | 10/2005 | Kuiper et al. | 623/17.11 |
| 2006/0064091 A1* | 3/2006 | Ludwig et al. | 606/61 |
| 2007/0073291 A1* | 3/2007 | Cordaro et al. | 606/61 |
| 2007/0233078 A1* | 10/2007 | Justis et al. | 606/61 |
| 2007/0250061 A1* | 10/2007 | Chin et al. | 606/61 |
| 2007/0270832 A1* | 11/2007 | Moore | 606/61 |
| 2007/0276374 A1* | 11/2007 | Broman et al. | 606/61 |
| 2008/0071274 A1* | 3/2008 | Ensign | 606/61 |
| 2008/0097441 A1* | 4/2008 | Hayes et al. | 606/64 |
| 2008/0119858 A1* | 5/2008 | Potash | 606/73 |
| 2008/0177318 A1* | 7/2008 | Veldman et al. | 606/256 |
| 2008/0221622 A1* | 9/2008 | Triplett et al. | 606/264 |
| 2008/0306513 A1* | 12/2008 | Winslow et al. | 606/246 |
| 2008/0306527 A1* | 12/2008 | Winslow et al. | 606/246 |
| 2008/0312692 A1* | 12/2008 | Brennan et al. | 606/246 |
| 2009/0024169 A1* | 1/2009 | Triplett et al. | 606/248 |
| 2009/0030463 A1* | 1/2009 | Samudrala et al. | 606/250 |
| 2009/0036934 A1* | 2/2009 | Biedermann et al. | 606/301 |
| 2009/0069852 A1* | 3/2009 | Farris et al. | 606/301 |
| 2009/0105760 A1* | 4/2009 | Frey | 606/246 |
| 2009/0118772 A1* | 5/2009 | Diederich et al. | 606/301 |
| 2009/0216277 A1* | 8/2009 | Tornier et al. | 606/250 |
| 2009/0254125 A1* | 10/2009 | Predick | 606/264 |
| 2009/0264926 A1* | 10/2009 | Taylor et al. | 606/246 |
| 2009/0299411 A1* | 12/2009 | Laskowitz et al. | 606/246 |
| 2010/0030270 A1* | 2/2010 | Winslow et al. | 606/254 |
| 2010/0036417 A1* | 2/2010 | James et al. | 606/246 |
| 2010/0036432 A1* | 2/2010 | Ely | 606/301 |
| 2010/0036436 A1* | 2/2010 | Winslow et al. | 606/305 |
| 2010/0042152 A1 | 2/2010 | Semler et al. | |
| 2010/0057131 A1* | 3/2010 | Ely et al. | 606/250 |
| 2010/0057135 A1* | 3/2010 | Heiges et al. | 606/301 |
| 2010/0057136 A1* | 3/2010 | Heiges et al. | 606/301 |
| 2010/0094345 A1* | 4/2010 | Saidha et al. | 606/250 |
| 2010/0160981 A1* | 6/2010 | Butler et al. | 606/308 |
| 2010/0222822 A1* | 9/2010 | Farris et al. | 606/264 |
| 2010/0280552 A1* | 11/2010 | Lee | 606/250 |
| 2010/0298884 A1* | 11/2010 | Faizan et al. | 606/266 |
| 2011/0106178 A1* | 5/2011 | Schwab | 606/308 |
| 2011/0137345 A1* | 6/2011 | Stoll et al. | 606/251 |
| 2011/0178558 A1* | 7/2011 | Barry | 606/302 |
| 2011/0213419 A1* | 9/2011 | Richelsoph | 606/264 |
| 2011/0218579 A1* | 9/2011 | Jackson | 606/305 |
| 2012/0095510 A1* | 4/2012 | Nihalani | 606/250 |
| 2012/0095511 A1* | 4/2012 | Nihalani | 606/250 |
| 2012/0123478 A1* | 5/2012 | Winslow et al. | 606/264 |
| 2012/0150230 A1* | 6/2012 | Felix et al. | 606/250 |
| 2012/0226316 A1* | 9/2012 | Dant et al. | 606/250 |
| 2012/0253400 A1* | 10/2012 | Clark et al. | 606/264 |
| 2012/0253401 A1* | 10/2012 | Clark et al. | 606/264 |
| 2012/0253402 A1* | 10/2012 | McLean | 606/264 |
| 2012/0277806 A1* | 11/2012 | Smith et al. | 606/308 |
| 2012/0283778 A1* | 11/2012 | Yeh | 606/250 |
| 2013/0023932 A1* | 1/2013 | Helgerson | 606/247 |
| 2013/0103092 A1* | 4/2013 | Ballard | 606/265 |
| 2013/0172934 A1* | 7/2013 | Walker et al. | 606/252 |
| 2013/0184759 A1* | 7/2013 | Rinehart et al. | 606/266 |
| 2013/0325069 A1* | 12/2013 | Pereiro de Lamo et al. | 606/263 |
| 2014/0012333 A1* | 1/2014 | Tornier et al. | 606/308 |
| 2014/0018866 A1* | 1/2014 | Jankovic et al. | 606/308 |
| 2014/0180338 A1* | 6/2014 | Triplett | 606/247 |

* cited by examiner

PERCUTANEOUS MODULAR HEAD-TO-HEAD CROSS CONNECTOR

FIELD OF THE INVENTION

The present disclosure relates to a surgical screw system comprising modular head-to-head cross connectors for use with implantation rods, and related methods of using a surgical screw system comprising modular head-to-head cross connectors with implantation rods. In an embodiment, the system may allow true percutaneous delivery through the spinous ligament.

BACKGROUND OF THE INVENTION

The spinal column of bones is highly complex anatomical structure that includes over 20 bones coupled to one another, housing and protecting critical elements of the nervous system having innumerable peripheral nerves and circulatory bodies in close proximity. Despite its complexity, the spine is a highly flexible structure, capable of a high degree of curvature and twist in nearly every direction. The more than 20 discrete bones of an adult human spinal column are anatomically categorized as one of four classifications—cervical, thoracic, lumbar, or sacral—and are coupled together sequentially to one another by a tri-joint complex that consists of an anterior disc and two posterior facet joints. The anterior discs of adjacent bones are cushioned by cartilage spacers referred to as intervertebral discs or vertebrae. The cervical portion of the spine comprises the top of the spine up to the base of the skull and includes the first seven vertebrae. The intermediate 12 bones are thoracic vertebrae, and connect to the lower spine comprising the 5 lumbar vertebrae. The base of the spine comprises sacral bones, including the coccyx. With its complex nature, however, there is also an increased likelihood that surgery may be needed to correct one or more spinal pathologies.

Genetic or developmental irregularities, trauma, chronic stress, tumors and disease can result in spinal pathologies that either limit this range of motion or that threaten critical elements of the nervous system housed within the spinal column. A variety of systems have been disclosed in the art which achieve this immobilization by implanting artificial assemblies in or on the spinal column. These assemblies may be classified as anterior, posterior, or lateral implants. Lateral and anterior implants are generally coupled to the anterior portion of the spine that is in the sequence of vertebral bodies. Posterior implants generally comprise pairs of rods, which are aligned along the axis that the bones are to be disposed, and that are then attached to the spinal column by hooks that couple to the lamina, hooks that attach to the transverse processes, or by screws that are inserted through pedicles. The orientation of each of these rods, however, are often limited by the alignment of the one or more screws they are affixed to.

Therefore, it is desirable, during surgical implantation of such posterior devices, to have a modular head-to-head cross connector that allows for percutaneous delivery, independent alignment between pairs of rods and fastener screw, and improved reliability, durability, and ease of installment of said devices.

BRIEF SUMMARY

Disclosed herein is a surgical screw system comprising modular head-to-head cross connectors or modular construct extensions for use with implantation rods, and related methods of using a surgical screw system comprising modular head-to-head cross connectors with implantation rods. The surgical screw system allows for percutaneous delivery of the system. The system may comprise a fastener element comprising an orbital head, wherein the fastener element is operable to be driven into a bone in a first orientation. A first U-shaped body may be operable to receive the orbital head of the fastener element in a proximal end and may be operable to receive a first rod in a first rod receiving channel in a distal end. A first compression element comprising an orbital head may be operable to be driven adjacent to and against the first rod in the first rod receiving channel, thereby engaging the first rod against the orbital head of the fastener element in a second orientation independent of the first orientation of the fastener element. A second U-shaped body may be operable to receive the orbital head of the first compression element in a proximal end and may be operable to receive a second rod in a second rod receiving channel in a distal end. A second compression element may be operable to be driven adjacent to and against the second rod in the second rod receiving channel, thereby engaging the second rod against the orbital head of the first compression element in a third orientation independent of the second orientation of the first rod and independent of the first orientation of the fastener element. Additional fastener elements, U-shaped bodies, and compression elements may be used in combination in order to allow for more than two levels of rods to be used in the modular head-to-head cross connector system.

BRIEF DESCRIPTION OF THE DRAWINGS

Embodiments are illustrated by way of example in the accompanying figures, in which like reference numbers indicate similar parts, and in which.

DETAILED DESCRIPTION

For purposes of describing and claiming the present disclosure, the term "interference fit" in intended to refer to physical contact between two or more components and may include a slip fit, a ball-joint fit, or similar fit between two or more components.

Figure 1:
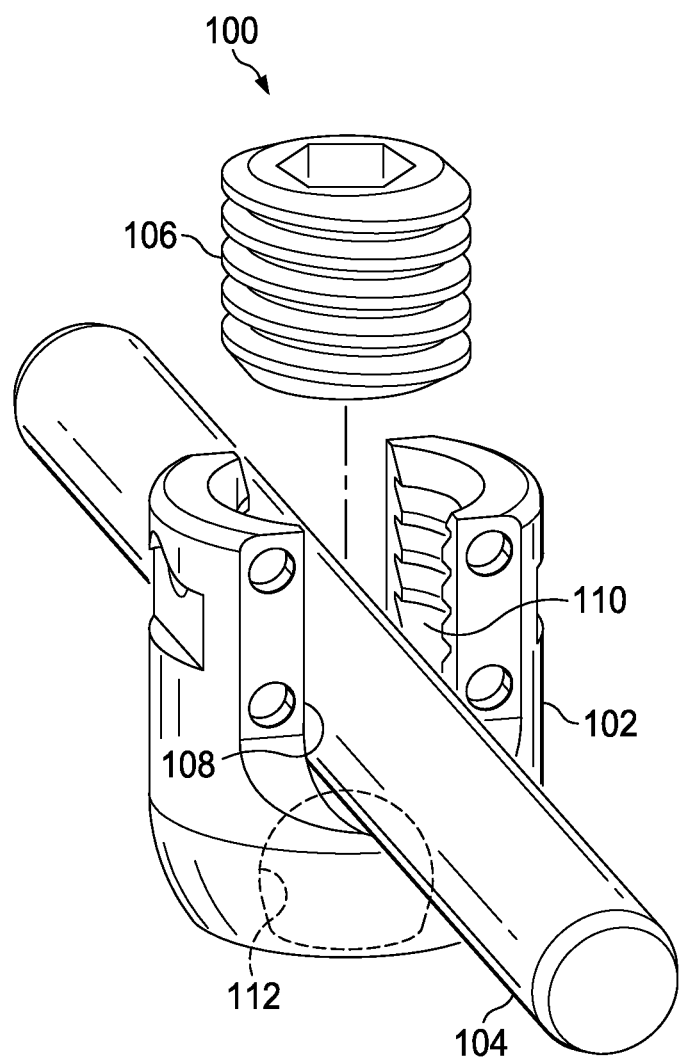
FIG. 1 depicts a prior art system for connecting a fastener element (e.g., a pedicle screw) relative to a rod for vertebral fixation.

FIG. 1 depicts a prior art connection system 100 for connecting a fastener element (e.g., a pedicle screw, not shown) relative to a rod 104 for vertebral fixation. Connection system 100 may comprise a U-shaped body 102, the rod 104, and a compression element 106. The rod 104 may be shaped to fit within the U-shaped body 102 at a rod receiving channel 108 with a slip fit. After the rod 104 is received within the rod receiving channel 108, the compression element 106 may be threaded into the U-shaped body 102 and mate with internal threads 110 of the U-shaped body 102. The compression element 106 may clamp the rod 104 against an orbital head of the fastener element when the fastener element is received into an orbital recess 112 of the U-shaped body 102. The U-shaped body 102 may be operable to rotate about the orbital head of the fastener element received into the orbital recess 112 in order to allow multi-axial rotation of the rod 104 relative to the fastener element. The fastener element and the U-shaped body 102 may comprise separate components or may comprise a single component wherein the fastener element is operable to rotate independently of the U-shaped body 102.

Figure 2:
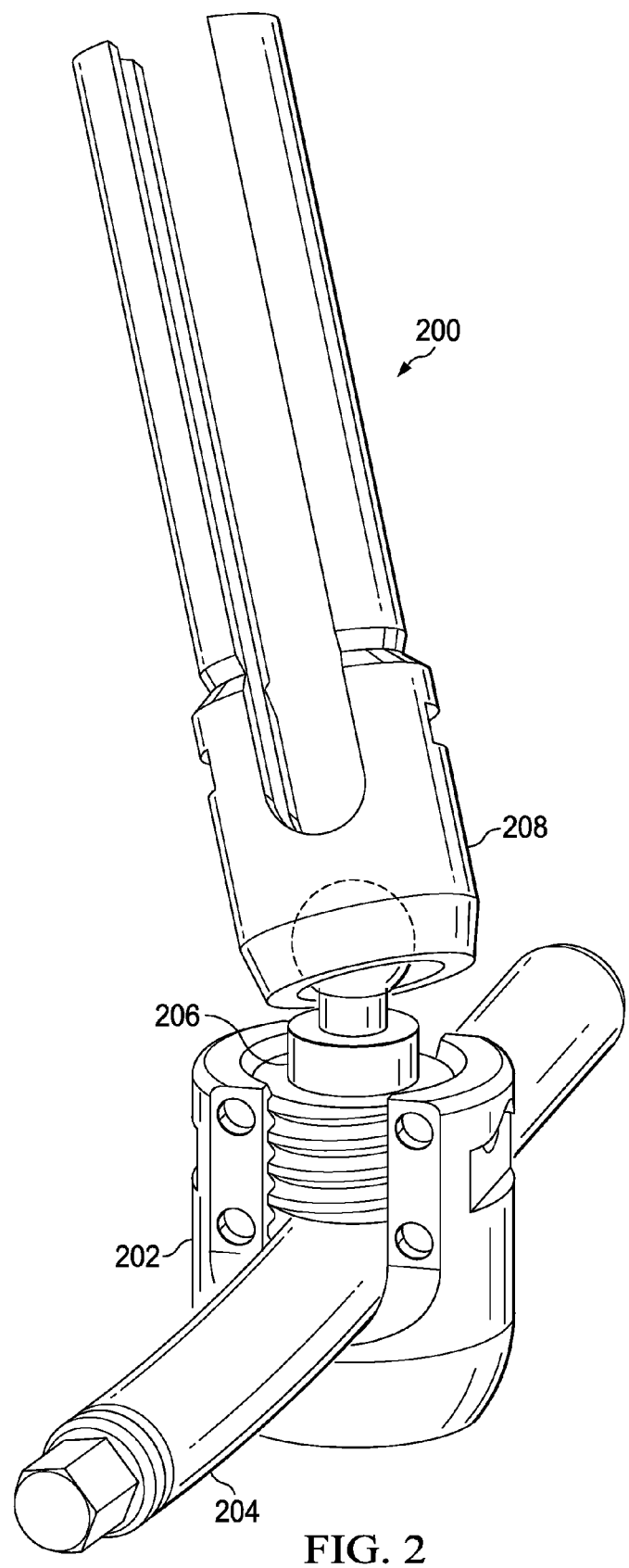
FIG. 2 depicts an elevational view of a modular head-to-head cross connecting system for percutaneous delivery, in accordance with one embodiment of the present disclosure.

FIG. 2 depicts an elevational view of a modular head-to-head cross connecting system 200 for percutaneous delivery, in accordance with one embodiment of the present disclosure. The modular head-to-head cross connecting system 200 may comprise a first U-shaped body 202, a rod 204, a modular compression element 206, and a second U-shaped body 208. Each of the components of the modular head-to-head cross connecting system 200 will be described in more detail in relation to corresponding FIGS. 3-10.

Figure 3:
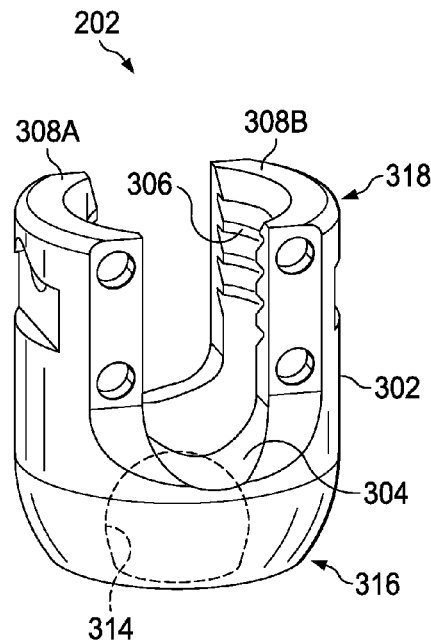
FIG. 3 depicts an elevational view of a first U-shaped body of the modular head-to-head cross connecting system of FIG. 2, in accordance with one embodiment of the present disclosure.

FIG. 3 depicts an elevational view of the first U-shaped body 202 of the modular head-to-head cross connecting system of FIG. 2, in accordance with one embodiment of the present disclosure. The first U-shaped body 202 may comprise a body 302 comprising a rod receiving channel 304, a first body side 308A, and a second body side 308B. The rod receiving channel 304 may be located at a distal end 318 and may define the first and second body sides 308A, 308B. The first and second body sides 308A, 308B may comprise internal threads 306 located proximate to the rod receiving channel 304 and configured to receive the rod 204 and the modular compression element 206, as shown in FIG. 2 and described in more detail in FIGS. 7-8.

The body 302 may further comprise an internal orbital recess 314 proximate to a proximal end 316 and opposite the rod receiving channel 304. The internal orbital recess 314 may be operable to receive an orbital head of a fastener element (e.g., pedicle screw, not shown). The first U-shaped body 202 may be operable to rotate about the orbital head of the fastener element (not shown) received into the orbital recess 314 in order to allow multi-axial rotation of the body 302 and a rod (not shown) relative to the fastener element.

The first U-shaped body 202 may further comprise first and second removable arms (not shown) operable to be removed from the body 302 at creases proximate to the intersection of the first and second removable arms and the body 302. The first and second removable arms may be located proximate to the distal end 318.

Figure 4:
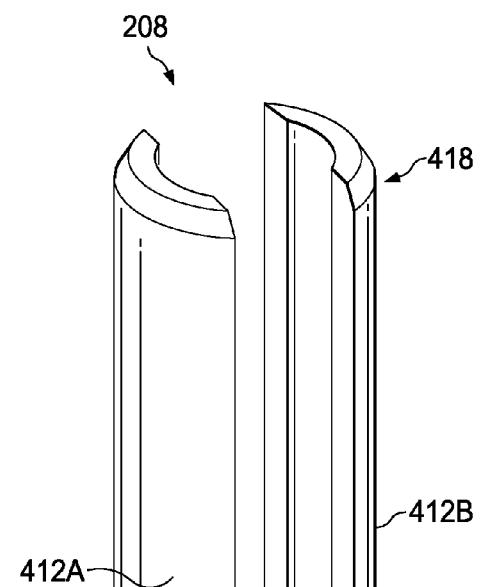
FIG. 4 depicts an elevational view of a second U-shaped body of the modular head-to-head cross connecting system of FIG. 2, in accordance with one embodiment of the present disclosure.

FIG. 4 depicts an elevational view of the second U-shaped body 208 of the modular head-to-head cross connecting system of FIG. 2, in accordance with one embodiment of the present disclosure. Like the first U-shaped body 202, the second U-shaped body 208 may comprise a body 402 comprising a rod receiving channel 404, a first body side 408A, and a second body side 408B. The rod receiving channel 404 may be located at a distal end 418 and may define the first and second body sides 408A, 408B. The first and second body sides 408A, 408B may comprise internal threads 406 located proximate to the rod receiving channel 304 and configured to receive the rod 204 and a non-modular compression element, as described in more detail in FIGS. 7-8.

The body 402 may further comprise an internal orbital recess 404 proximate to a proximal end 416 and opposite the rod receiving channel 404. The internal orbital recess 414 may be operable to receive an orbital head of the modular compression element 206, as shown in FIG. 2. The second U-shaped body 208 may be operable to rotate about the orbital head of the modular compression (not shown) element received into the orbital recess 414 in order to allow multi-axial rotation of the body 402 and a rod (not shown) relative to the modular compression element.

The second U-shaped body 208 may further comprise first and second removable arms 412A, 412B operable to be removed from the body 402 at creases 410A, 410B. The first and second removable arms 412A, 412B may be located proximate to the distal end 418.

Figure 5:
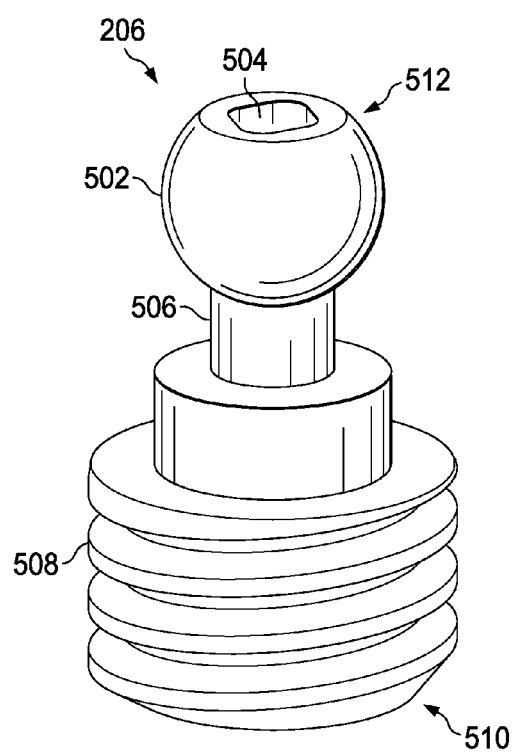
FIG. 5 depicts an elevational view of a modular compression element of the modular head-to-head cross connecting system of FIG. 2, in accordance with one embodiment of the present disclosure.

FIG. 5 depicts an elevational view of the modular compression element 206 of the modular head-to-head cross connecting system of FIG. 2, in accordance with one embodiment of the present disclosure. The modular compression element 206 may comprise an orbital head 502 located at a distal end 512 connected to a compression element body 506 at a proximal end 510. Part or all of the compression element body 506 may comprise threads 508 about the compression element body 506. The threads 508 may allow the modular compression element 206 to mate with the threads of the first and second body sides of the first U-shaped body shown in FIG. 3.

The orbital head 502 of the modular compression element 206 may further comprise a driving recess 504 operable to receive a driving instrument (not shown). Although shown as a square-shaped driving recesses 504 in FIG. 5, the driving recess 504 may be hex-shaped, Philips-head shaped, flat-head-shaped, or any other shape operable to receive a driving instrument.

Figures 6, 7:
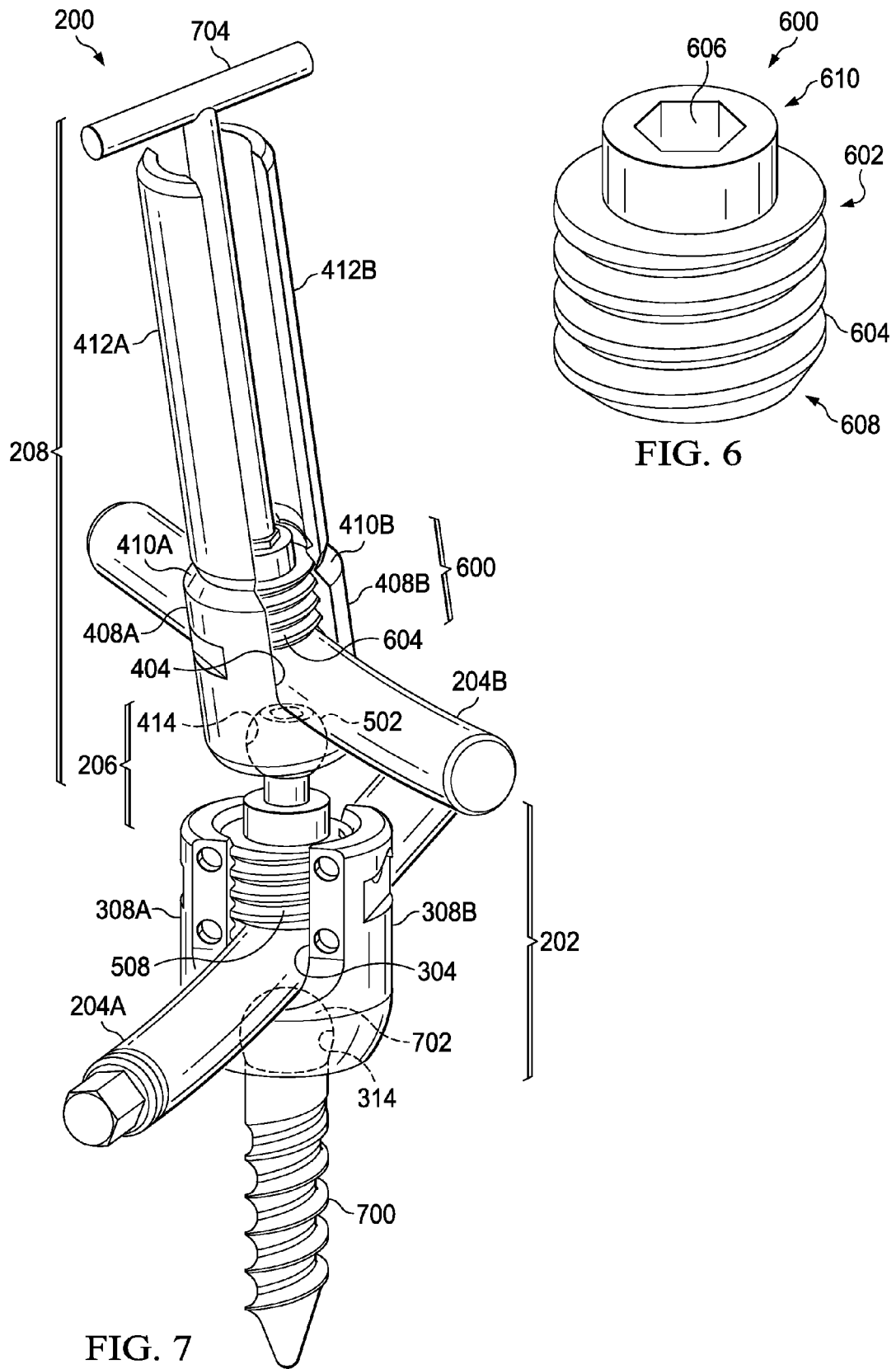
FIG. 6 depicts an elevational view of a non-modular compression element, in accordance with one embodiment of the present disclosure.
FIG. 7 depicts an elevational view of a modular head-to-head cross connecting system for percutaneous delivery with a second rod set in the second U-shaped body, in accordance with one embodiment of the present disclosure.

FIG. 6 depicts an elevational view of a non-modular compression element 600, in accordance with one embodiment of the present disclosure. The non-modular compression element 600 may comprise a compression element body 602 comprising a proximal end 608 and a distal end 610. Part or all of the compression element body 602 may comprise threads 604 about the compression element body 602. The threads 604 may allow the non-modular compression element 600 to mate with the threads of the first and second body sides of the second U-shaped body shown in FIG. 4.

The distal end 610 of the non-modular compression element 600 may further comprise a driving recess 606 operable to receive a driving instrument (not shown). Although shown as a square-shaped driving recesses 606 in FIG. 6, the driving recess 606 may be a hex-shaped, Philips-head shaped, flat-head-shaped, or any other shape operable to receive a driving instrument.

Figure 8:
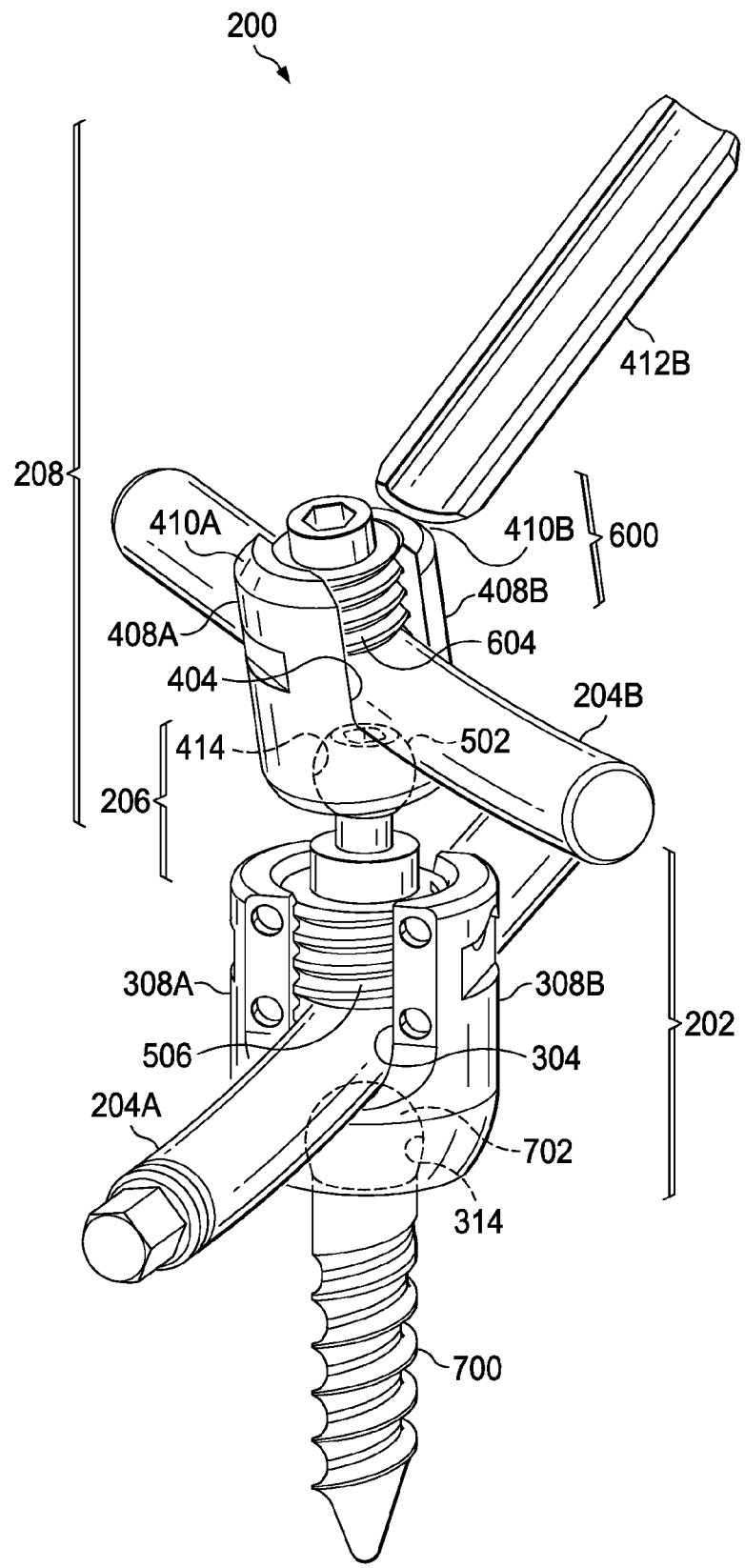
FIG. 8 depicts an elevational view of FIG. 7 with a first arm removed from the second U-shaped body removed and a second arm of the second U-shaped body in the process of being removed, in accordance with one embodiment of the present disclosure.

FIG. 7 depicts an elevational view of the modular head-to-head cross connecting system 200 for percutaneous delivery with a first rod 204A received in the first U-shaped body 202 and a second rod 204B received in the second U-shaped body 208, in accordance with one embodiment of the present disclosure. FIG. 8 depicts an elevational view of FIG. 7 with the first removable arm 412A removed from the second U-shaped body 208 and the second removable arm 412A of the second U-shaped body 208 detached from the second U-shaped body 208, in accordance with one embodiment of the present disclosure.

In operation, and as shown in FIG. 7, a fastener element 700 may comprise an orbital head 702 and may be a threaded pedicle bone screw. The fastener element 700 may be driven into a bone such as a pedicle in a first orientation with a driving element (not shown) during a surgical procedure. After the fastener element 700 has been driven into the pedicle and set in its desired location, the first U-shaped body 202 may be placed or "snapped" over the orbital head 702 so that the orbital recess 314 of the first U-shaped body 202 has an interference fit with the orbital head 702 of the fastener element 700. In an embodiment, the interference fit between the fastener element 700 and the first U-shaped body 202 may be a ball-joint fit.

Alternatively, the fastener element 700 may be received through the distal end of the first U-shaped body 202 before the fastener element 700 is driven into the bone so that the first U-shaped body 202 receives the orbital head 702 of the fastener element 700 in the orbital recess 314 in the proximal end of the first U-shaped body 202. The fastener element 700 may then be driven into the bone in the first orientation with a driving element (not shown) during a surgical procedure.

After the fastener element 700 is driven into the bone in the first orientation and the orbital head 702 of fastener element 700 is received in the first U-shaped body 202, the first rod 204A may be received into the rod receiving channel 304 of the first U-shaped body 202. Before the modular compression element 206 of FIG. 5 is driven down onto the first rod 204A, as discussed in more detail below, the first rod 204A may be operable to slide along its axis within the rod receiving channel 304 and independent of the first U-shaped body 202, and both the first U-shaped body 202 and the first rod 204A may be operable to pivot in unison relative to the orbital head 702 of the fastener element 700. The interference fit allows the first U-shaped body 202 to be rotated about the orbital head 702 of the fastener element 700 so that the first rod 204A may be aligned in a second orientation independent of the first orientation of the fastener element 700. In an embodiment, the first U-shaped body 202 may be circumferentially pivotable on the orbital head 702 of the fastener element 700 around a longitudinal axis defined by the first orientation of the fastener element 700 and/or may have a desired degree of angular freedom (e.g., approximately 26° from the longitudinal axis of the fastener element 700 or 52° from one side to the other).

After the second orientation of the first rod 204A has been approximately set as desired, the modular compression element 206 may be operable to be inserted into the rod receiving channel 304 of the first U-shaped body 202. As previously discussed, the modular compression element 206 may be operable to be driven down onto the first rod 204A with a driving element (not shown). The threads 508 of the modular compression element 206 may be operable mate with the internal threads 306 of the first and second body sides 308A, 308B of the first U-shaped body 202, allowing the first rod 204A to be operable to be driven against an end of the rod receiving channel 304. When the first rod 204A has been driven adjacent to the end of the rod receiving channel 304, the distal end of the modular compression element 206 may be in an interference fit with a first surface of the first rod 204A and a second surface of the first rod 204A may be in an interference fit with a surface of the orbital head 702 of the fastener element 700.

Before the modular compression element 206 is fully driven down onto the first rod 204A, the snug interference fit between the modular compression element 206 and the first rod 204A and between the first rod 204A and the orbital head 702 may be a slip fit that allows minor displacement of the first rod 204A slidably along its axis relative to the first U-shaped body 202 and allow the first rod 204A and the first U-shaped body 202 minor pivotable adjustment relative to the fastener 700 when setting the second orientation of the first rod 204A. After the desired second orientation has been achieved, the modular compression element 206 may be further driven against the first rod 204A so that the second orientation of the first rod 204A relative to the first orientation of the fastener element 700 is set and minor adjustments to the second are no longer possible.

Although not shown in FIG. 3 or 7, the first U-shaped body 202 may optionally comprise first and second removable arms (corresponding to the first and second removable arms 512A, 512B of the second U-shaped body 208 in FIG. 4). After the second orientation of the first rod 204A has been set, the first and second removable arms may be detached from the first U-shaped body 202 at first and second creases.

Next, the second U-shaped body 208 may be placed or "snapped" over the orbital head 502 of the modular compression element 206 so that the orbital recess 414 of the second U-shaped body 208 has an interference fit with the orbital head 502 of modular compression element 206. After the second U-shaped body 208 is mated with the modular compression unit 206, the second rod 204B may be received into the rod receiving channel 404 of the second U-shaped body 208.

Alternatively, the orbital head 502 of the modular compression element 206 may be received in the orbital recess 414 of the second U-shaped body 208 before the modular compression element 206 is driven into the first U-shaped body 202 and against the first rod 204A. The modular compression element 206 may then be driven adjacent to and against the first rod 204A with a driving element (not shown) during a surgical procedure.

The interference fit between the modular compression element 206 and the second U-shaped body 208 may be a ball-joint fit that allows the second U-shaped body 208 and the second rod 204B to pivot about the orbital head 502 of the modular compression element 206 so that the second rod 204B may be aligned in a third orientation independent of the second orientation of the first rod 204A and independent of the first orientation of the fastener element 700. In an embodiment, the second U-shaped body 208 may be circumferentially pivotable on the orbital head 502 of the modular compression element 206 around a longitudinal axis defined from the proximal end to the distal end of the modular compression element 206 and/or may have a desired degree of angular freedom (e.g., approximately 26° from the longitudinal axis of the modular compression element 206 or 52° from one side to the other).

Before the non-modular compression element 600 of FIG. 6 is driven down onto the second rod 204B, as discussed in more detail below, the second rod 204B may be operable to slide along its axis within the rod receiving channel 404 independent of the second U-shaped body 208, and both the second U-shaped body 208 and the second rod 204B may be operable to pivot in unison relative to the modular compression element 206 in order to set the third orientation of the second rod 204B.

After the third orientation of the second rod 204B is approximately set as desired, the non-modular compression element 600 may be operable to be inserted into the rod receiving channel 404 of the second U-shaped body 208. As previously discussed, the non-modular compression element 600 may be operable to be driven down onto the second rod 204B with a driving element 704. Although not shown in FIG. 7, the driving element 704 may also be operable to drive the fastener element 700 and the modular compression element 206. The threads 604 of the non-modular compression element 600 may be operable mate with the internal threads 406 of the first and second body sides 408A, 408B of the second U-shaped body 208, allowing the second rod 204B to be operable to be driven against an end of the rod receiving channel 404. When the second rod 204B has been driven adjacent to the end of the rod receiving channel 404, the distal end of the non-modular compression element 600 may be in an interference fit with a first surface of the second rod 204B and a second surface of the second rod 204B may be in an interference fit with a surface of the orbital head 502 of the modular compression element 206.

Before the non-modular compression element 600 is fully driven down onto the second rod 204B, the snug interference fit between the non-modular compression element 600 and the second rod 204B and between the second rod 204B and the orbital head 502 may be a slip fit that allows minor displacement of the second rod 204B along its axis relative to the second U-shaped body 208 and may allow the second rod 204B and the second U-shaped body 208 minor pivotable adjustment relative to the modular compression element 206 when setting the third orientation of the second rod 204B. After the desired third orientation of the second rod 204B has been achieved, the non-modular compression element 600 may be further driven against the second rod 204B so that the third orientation of the second rod 204B is set, and minor adjustments of third orientation of the second rod 204B are no longer possible. Advantageously, each of the first, second, and third orientations may be set independently of each other.

As shown in FIG. 8, after the third orientation of the second rod 204B has been set and the driving element 704 has been removed, the first and second removable arms 412A, 412B may be detached from the second U-shaped body 208 at the first and second creases 410A, 410B. In FIG. 8, the first removable arm 412A has been removed from the second U-shaped body 208 and the second removable arm 412B is in the process of being removed from the second U-shaped body 208 and has been bent approximately 45° at the second crease 410B relative to the body 402 of the second U-shaped body 208. By removing the first and second removable arms 412A, 412B, the total depth of the modular head-to-head cross connecting system 200 may be advantageously reduced.

Although FIGS. 7 and 8 depict only one U-shaped body affixed to each rod, it is to be understood that any number of U-shaped bodies can be affixed to each rod and that more than two U-shaped bodies may be stacked on top of each other in order to allow for more than two levels of rods to be used.

Figure 9:
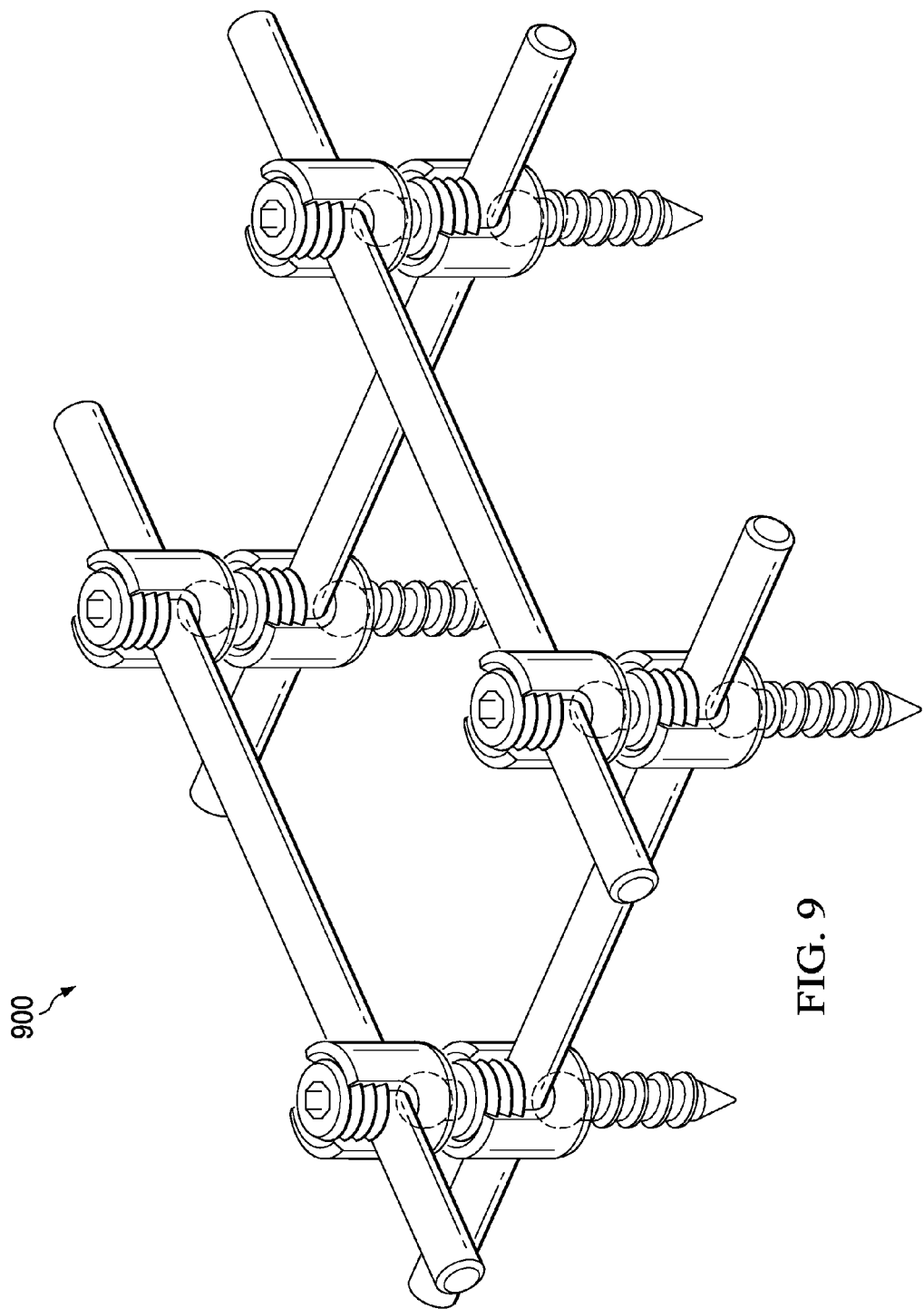
FIG. 9 depicts an elevational view of a modular head-to-head cross connecting system comprising four rods set in a square arrangement, in accordance with one embodiment of the present disclosure.

FIG. 9 depicts an elevational view of a modular head-to-head cross connecting system 900 comprising four rods set in a rectangular arrangement, in accordance with one embodiment of the present disclosure. Using a combination of rods, U-shaped bodies, modular compression elements, and non-modular compression elements, the first orientations of the fastener elements in the pedicle bodies (not shown) may be independent of the second orientations of the rods proximate to the fastener elements, which may be independent of the third orientations of the rods distant to the fastener elements.

Figure 10:
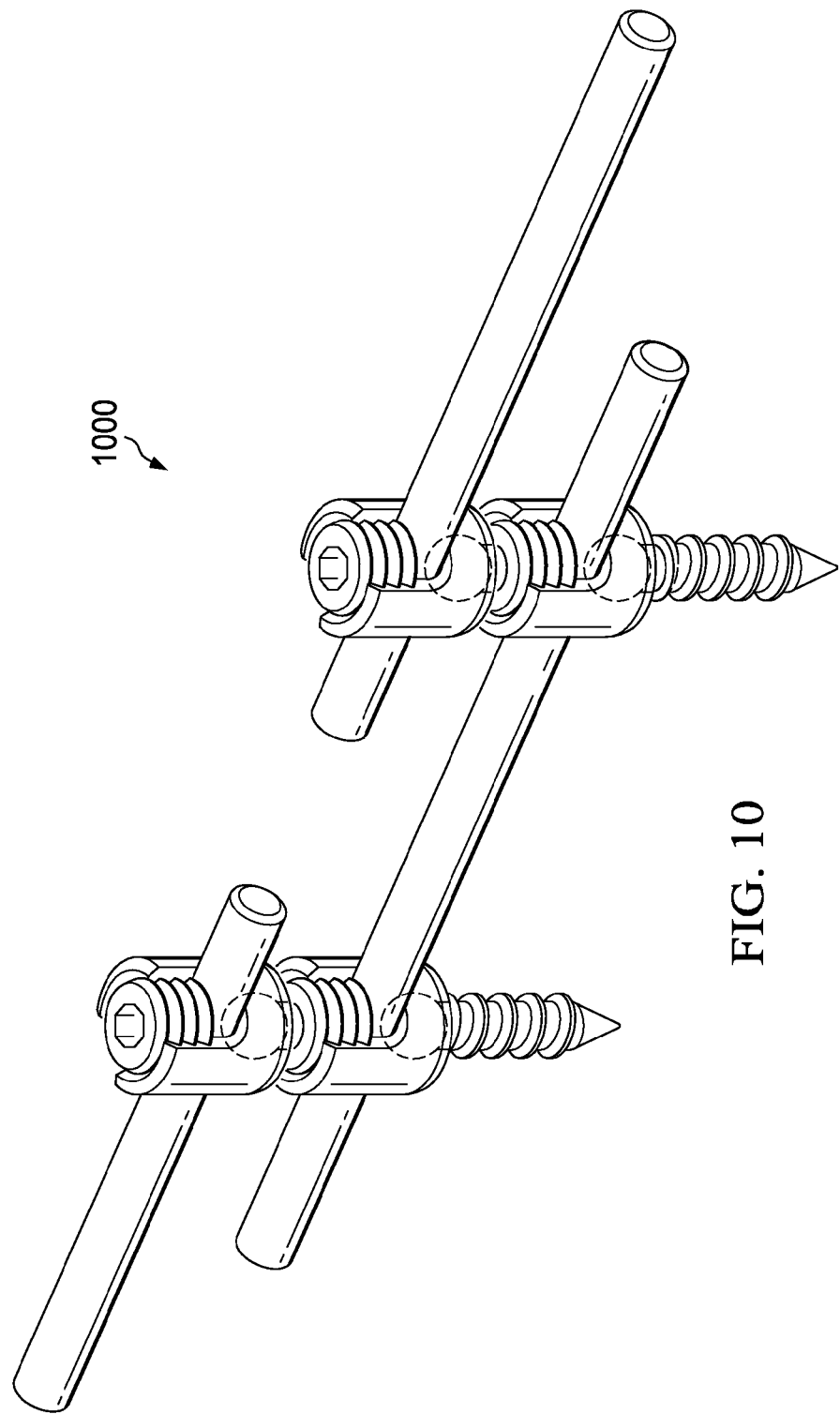
FIG. 10 depicts an elevational view of a modular construct extension system comprising two rods set in an in-line arrangement, in accordance with one embodiment of the present disclosure.

FIG. 10 depicts an elevational view of a modular construct extension system 1000 comprising three rods set in an in-line arrangement, in accordance with one embodiment of the present disclosure. In the modular construct extension arrangement, one or more extension rods may be used to extend a first rod, for example to adjacent spinal segments or the pelvis. Each extension rod may be affixed proximally or distally to a first construct comprising a combination of rods, U-shaped bodies, modular compression elements, and non-modular compression elements. While not shown in FIG. 10, each extension rod may be affixed to a second construct comprising a combination of rods, U-shaped bodies, modular compression elements, and non-modular compression elements, wherein the first construct and the second construct are located at opposite ends of the extension rod. The one ore more extension rods may be implanted at the same time as the first rod or at a later time via either traditional, "open" surgical techniques or via minimally invasive surgical techniques.

Various sized rods, U-shaped bodies, fastener elements, modular compression elements, and non-modular compression elements may be employed in the embodiments depicted in FIGS. 2-10. In an embodiment, one or more rods may be approximately 5.5 mm diameter rods, while in another embodiment one or more rods may be approximately 3.0-3.5 mm diameter rods. The length of the rods may be determined by the desired application of the modular head-to-head cross connector system. Advantageously, the disclosed embodiments allow for percutaneous delivery of the modular head-to-head cross connector system.

One or more components of the modular head-to-head cross connecting systems disclosed herein may be made from any of the following materials: (a) any biocompatible material (which biocompatible material may be treated to permit bone ingrowth or prohibit bone ingrowth); (b) a plastic; (c) a fiber; (d) a polymer; (e) a metal (e.g., a pure metal such as titanium and/or an alloy such as Ti—Al—Nb, TI-6Al-4V, stainless steel); or (f) any combination thereof.

While various embodiments in accordance with the principles disclosed herein have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

It will be understood that the principal features of this disclosure can be employed in various embodiments without departing from the scope of the disclosure. Those skilled in the art will recognize, or be able to ascertain using no more than routine experimentation, numerous equivalents to the specific procedures described herein. Such equivalents are considered to be within the scope of this disclosure and are covered by the claims.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

What is claimed is:

1. A low profile modular head-to-head cross connector system for use with implantation rods, the system comprising:
    a fastener element comprising an orbital head, wherein the fastener element is operable to be driven into a bone in a first orientation;
    a first U-shaped body operable to receive the orbital head of the fastener element in a proximal end and operable to receive a first rod in a first rod receiving channel in a distal end;
    a first compression element comprising an rigid orbital head, wherein the first compression element is operable to be driven adjacent to and against the first rod in the first rod receiving channel, thereby engaging the first rod against the orbital head of the fastener element in a second orientation independent of the first orientation of the fastener element;
    a second U-shaped body operable to receive the rigid orbital head of the first compression element in a proximal end and operable to receive a second rod in a second rod receiving channel in a distal end; and
    a second compression element operable to be driven adjacent to and against the second rod in the second rod receiving channel, thereby engaging the second rod against the rigid orbital head of the first compression element in a third orientation independent of the second orientation of the first rod and independent of the first orientation of the fastener element.

2. The modular head-to-head cross connector system of claim 1, wherein the first rod receiving channel intersects the first U-shaped body at the distal end and ends before the proximal end at an end of the first rod receiving channel.

3. The modular head-to-head cross connector system of claim 2, wherein the first U-shaped body further comprises first and second body sides defined by the first rod receiving channel.

4. The modular head-to-head cross connector system of claim 3, wherein internal surfaces of the first and second body sides proximate to the first rod receiving channel of the first U-shaped body are threaded.

5. The modular head-to-head cross connector system of claim 4, wherein the first U-shaped body further comprises an orbital recess in the proximal end, wherein the orbital recess is operable to receive the orbital head of the fastener element through an interference fit.

6. The modular head-to-head cross connector system of claim 5, wherein a distal end of the orbital recess of the first U-shaped body is adjacent to the end of the first rod receiving channel.

7. The modular head-to-head cross connector system of claim 6, wherein the orbital head of the first compression element is at a distal end.

8. The modular head-to-head cross connector system of claim 7, wherein the first compression element comprises a threaded body at a proximal end operable to mate with the threaded internal surfaces of the first and second body sides of the first U-shaped body.

9. The modular head-to-head cross connector system of claim 8, wherein the interference fit between the orbital head of the fastener element and the orbital recess of the first U-shaped body is operable to allow the first U-shaped body to pivot about the orbital head so that the first rod is operable be aligned in the second orientation independent of the first orientation of the fastener element.

10. The modular head-to-head cross connector system of claim 9, wherein when the first compression element is driven adjacent to the first rod, the first U-shaped body and the first rod are operable to pivot in unison relative to the orbital head of the fastener element and the first rod can be positioned along its axis within the first rod receiving channel independent of the first U-shaped body.

11. The modular head-to-head cross connector system of claim 10, wherein the first compression element is operable to be further driven against the first rod, thereby engaging the first rod against the orbital head of the fastener element, and thereby locking the second orientation of the first rod with respect to the first orientation of the fastener element and locking the position of the first rod along its axis within the first rod receiving channel.

12. The modular head-to-head cross connector system of claim 1, wherein the second rod receiving channel intersects the second U-shaped body at the distal end and ends before the proximal end at an end of the second rod receiving channel.

13. The modular head-to-head cross connector system of claim 12, wherein the second U-shaped body further comprises first and second body sides defined by the second rod receiving channel.

14. The modular head-to-head cross connector system of claim 13, wherein internal surfaces of the first and second body sides proximate to the second rod receiving channel of the second U-shaped body are threaded.

15. The modular head-to-head cross connector system of claim 14, wherein the second U-shaped body further comprises an orbital recess in the proximal end, wherein the orbital recess is operable to receive the orbital head of the first compression element through an interference fit.

16. The modular head-to-head cross connector system of claim 15, wherein a distal end of the orbital recess of the second U-shaped body is adjacent to the end of the second rod receiving channel.

17. The modular head-to-head cross connector system of claim 16, wherein the second compression element comprises a threaded body at a proximal end operable to mate with the threaded internal surfaces of the first and second body sides of the second U-shaped body.

18. The modular head-to-head cross connector system of claim 17, wherein the interference fit between the orbital head of the first compression element and the orbital recess of the second U-shaped body is operable to allow the second U-shaped body to pivot about the orbital head so that the second rod is operable be aligned in the third orientation independent of the first orientation of the fastener element and independent of the second orientation of the first rod.

19. The modular head-to-head cross connector system of claim 18, wherein when the second compression element is driven adjacent to the second rod, the second U-shaped body and the second rod are operable to pivot in unison relative to the orbital head of the first compression element and the second rod can be positioned along its axis within the second rod receiving channel independent of the second U-shaped body.

20. The modular head-to-head cross connector system of claim 19, wherein the second compression element is operable to be further driven against the second rod, thereby engaging the second rod against the orbital head of the first compression element, and thereby locking the third orientation of the second rod with respect to the second orientation of the first rod and the first orientation of the fastener element and locking the position of the second rod along its axis within the second rod receiving channel.

21. A low profile modular construct extension system for use with implantation rods, the system comprising:
   a fastener element comprising an orbital head, wherein the fastener element is operable to be driven into a bone in a first orientation;
   a first U-shaped body operable to receive the orbital head of the fastener element in a proximal end and operable to receive a first rod in a first rod receiving channel in a distal end;
   a first compression element comprising an rigid orbital head, wherein the first compression element is operable to be driven adjacent to and against the first rod in the first rod receiving channel, thereby engaging the first rod against the orbital head of the fastener element in a second orientation independent of the first orientation of the fastener element;
   a second U-shaped body operable to receive the rigid orbital head of the first compression element in a proximal end and operable to receive a second rod in a second rod receiving channel in a distal end; and
   a second compression element operable to be driven adjacent to and against the second rod in the second rod receiving channel, thereby engaging the second rod against the rigid orbital head of the first compression element in a third orientation, wherein the third orientation is independent of the first orientation of the fastener element, and wherein the third orientation is substantially parallel to the second orientation.

* * * * *